(12) United States Patent
Yang et al.

(10) Patent No.: US 10,695,008 B2
(45) Date of Patent: Jun. 30, 2020

(54) X-RAY IMAGING DEVICE AND METHOD

(71) Applicants: VATECH Co., Ltd., Gyeonggi-do (KR); VATECH EWOO Holdings Co., Ltd., Gyeonggi-do (KR)

(72) Inventors: Yong-Joo Yang, Gyeonggi-do (KR); Keun-Yeoung Kim, Gyeonggi-do (KR); Tae-Woo Kim, Gyeonggi-do (KR); Sung-Il Choi, Gyeonggi-do (KR)

(73) Assignees: VATECH Co. Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 232 days.

(21) Appl. No.: 15/570,321

(22) PCT Filed: Jul. 24, 2015

(86) PCT No.: PCT/KR2015/007728
§ 371 (c)(1),
(2) Date: Oct. 27, 2017

(87) PCT Pub. No.: WO2016/175386
PCT Pub. Date: Nov. 3, 2016

(65) Prior Publication Data
US 2018/0125434 A1 May 10, 2018

(30) Foreign Application Priority Data
Apr. 29, 2015 (KR) .................. 10-2015-0060370

(51) Int. Cl.
*A61B 6/03* (2006.01)
*A61B 6/00* (2006.01)
(Continued)

(52) U.S. Cl.
CPC ............. *A61B 6/03* (2013.01); *A61B 6/022* (2013.01); *A61B 6/032* (2013.01); *A61B 6/14* (2013.01);
(Continued)

(58) Field of Classification Search
None
See application file for complete search history.

(56) References Cited

U.S. PATENT DOCUMENTS 6,118,842 A 9/2000 Arai et al.
6,169,780 B1 1/2001 Yoshimura et al.
(Continued)

FOREIGN PATENT DOCUMENTS

CN 1214231 A 4/1999
CN 1446517 A 10/2003
(Continued)

OTHER PUBLICATIONS

European Patent Office, European Search Report of corresponding EP Patent Application No. 15890827.7, dated Dec. 14, 2018.
(Continued)

*Primary Examiner* — Edwin C Gunberg
(74) *Attorney, Agent, or Firm* — IP Legal Services, LLC

(57) ABSTRACT

The present invention provides an X-ray imaging device including an X-ray emitter and an X-ray detector rotating while facing each other with an imaging subject interposed therebetween, a device controller controlling the X-ray imaging device such that a first X-ray imaging is performed with a first dose in a partial section of a rotation locus of the X-ray emitter and the X-ray detector and a second X-ray imaging is performed with a second dose lower than the first dose in a remaining section, and an image processor pro-
(Continued)

ducing an X-ray image by receiving first and second X-ray image data of the first and the second X-ray imaging from the X-ray detector.

10 Claims, 3 Drawing Sheets

(51) Int. Cl.
*A61B 6/14* (2006.01)
*G06T 7/00* (2017.01)
*A61B 6/02* (2006.01)

(52) U.S. Cl.
CPC .......... *A61B 6/405* (2013.01); *G06T 7/0012* (2013.01); *G06T 7/97* (2017.01); *A61B 6/027* (2013.01); *A61B 6/542* (2013.01); *G06T 2207/10081* (2013.01); *G06T 2207/10116* (2013.01); *G06T 2207/30036* (2013.01)

(56) References Cited

U.S. PATENT DOCUMENTS

| | | | |
|---|---|---|---|
| 2003/0185343 | A1 | 10/2003 | Horiuchi |
| 2007/0030951 | A1 | 2/2007 | Park et al. |
| 2009/0041191 | A1 | 2/2009 | Suzuki et al. |
| 2009/0046833 | A1* | 2/2009 | Hirokawa ............ A61B 6/032 378/108 |
| 2009/0175562 | A1* | 7/2009 | Pan ..................... A61B 6/032 382/312 |
| 2009/0232274 | A1 | 9/2009 | Spartiotis et al. |
| 2009/0268867 | A1 | 10/2009 | Mori et al. |
| 2011/0064188 | A1 | 3/2011 | Suzuki et al. |
| 2011/0141255 | A1 | 6/2011 | Mori et al. |
| 2012/0093284 | A1 | 4/2012 | Takemoto et al. |
| 2013/0003914 | A1 | 1/2013 | Yin et al. |
| 2014/0140470 | A1 | 5/2014 | Cho |
| 2014/0321611 | A1 | 10/2014 | Cho |
| 2015/0010126 | A1 | 1/2015 | Rotondo et al. |
| 2015/0265237 | A1 | 9/2015 | Keeve et al. |
| 2015/0305696 | A1 | 10/2015 | Yamakawa et al. |

FOREIGN PATENT DOCUMENTS

| | | |
|---|---|---|
| CN | 1787780 A | 6/2006 |
| CN | 100563574 C | 12/2009 |
| CN | 102014753 A | 4/2011 |
| CN | 102014754 A | 4/2011 |
| CN | 102413770 A | 4/2012 |
| CN | 102551772 A | 7/2012 |
| CN | 103096804 A | 5/2013 |
| CN | 103829960 A | 6/2014 |
| CN | 104066376 A | 9/2014 |
| DE | 10 2012 219 269 A1 | 5/2014 |
| JP | 11-290309 A | 10/1999 |
| JP | 2003-290214 A | 10/2003 |
| JP | 2006-014822 A | 1/2006 |
| KR | 10-2014-0004433 A | 1/2014 |
| KR | 10-1412575 B1 | 6/2014 |

OTHER PUBLICATIONS

State Intellectual Property Office of People's Republic of China, Office Action of corresponding CN Patent Application No. 201580080802.0, dated Apr. 2, 2020.

* cited by examiner

X-RAY IMAGING DEVICE AND METHOD

CROSS REFERENCE TO RELATED APPLICATIONS

This application is a National Stage Patent Application of PCT International Patent Application No. PCT/KR2015/007728 (filed on Jul. 24, 2015) under 35 U.S.C. § 371, which claims priority to Korean Patent Application No. 10-2015-0060370 (filed on Apr. 29, 2015), the teachings of which are incorporated herein in their entireties by reference.

TECHNICAL FIELD

The present invention relates generally to an X-ray imaging device and an X-ray imaging method. More particularly, the present invention relates to an X-ray imaging device and an X-ray imaging method, wherein the X-ray imaging device is configured to selectively perform X-ray imaging in a partial section of a rotation locus of an X-ray emitter and an X-ray detector rotating while facing each other with an imaging subject interposed therebetween, thereby producing a multi-modality image.

BACKGROUND ART

In the field of dentistry, in order to obtain a modality X-ray image, such as a CT image, a panoramic image, and a cephalometric image, suitable for diagnostic purposes, the relevant X-ray imaging devices should be provided individually, or an X-ray imaging device in which these imaging devices are integrated should be provided.

As described above, conventionally, a separate X-ray imaging device or an integrated X-ray imaging device is required to produce a variety of modality images, and accordingly, there are problems such as an increase in device cost for producing a variety of modality images and a decrease in space utilization. Further, when using the integrated X-ray imaging device, the design and operation thereof become complicated.

As described above, in the conventional case, there is a problem in that the efficiency is low in producing a multi-modality image.

DISCLOSURE

Technical Problem

Accordingly, the present invention has been made keeping in mind the above problems occurring in the related art, and an object of the present invention is to provide a way to improve efficiency in producing multi-modality image.

Technical Solution

In order to achieve the above object, according to one aspect of the present invention, there is provided an X-ray imaging device including: an X-ray emitter and an X-ray detector rotating while facing each other with an imaging subject interposed therebetween; a device controller controlling the X-ray imaging device such that a first X-ray imaging is performed with a first dose in a partial section of a rotation locus of the X-ray emitter and the X-ray detector, and a second X-ray imaging is performed with a second dose lower than the first dose in a remaining section; and an image processor producing an X-ray image by processing first and second X-ray image data of the first and the second X-ray imaging from the X-ray detector.

Herein, the X-ray emitter may be turned off during the second X-ray imaging.

The partial section may be in a range of 60 to 300 degree angles relative to a front (0 degree angles) of the imaging subject based on the X-ray emitter, and the X-ray image may be a dental arch panoramic image of the imaging subject.

The partial section may be in a range of 300 to 60 degree angles and 120 to 240 degree angles relative to a front (0 degree angles) of the imaging subject based on the X-ray emitter, and the X-ray image may be a posteroanterior cephalometric image of the imaging subject.

The partial section may be in a range of 30 to 150 degree angles and 210 to 330 degree angles relative to a front (0 degree angles) of the imaging subject based on the X-ray emitter, and the X-ray image may be a lateral cephalometric image of the imaging subject.

The X-ray emitter may irradiate X-rays onto a partial area of an entire incident area of the X-ray detector.

The X-ray emitter may be configured to adjust a position of the partial area onto which the X-rays are irradiated, according to a location of the X-ray detector.

The X-ray detector may be configured such that an aspect ratio thereof is 1:2 or more and 1:10 or less.

The X-ray detector may be moved in a direction of the rotation locus or in a tangential direction of the rotation locus during at least a part of the rotation of the X-ray emitter and the X-ray detector.

A center of the rotation locus of the X-ray emitter and the X-ray detector may be moved during at least a part of the rotation of the X-ray emitter and the X-ray detector.

The modality image may be at least one of a dental arch panoramic image, a cephalometric image, a TMJ image, and a sinus image.

In order to achieve the above object, according to another aspect of the present invention, there is provided an X-ray imaging method including: disposing an X-ray emitter and an X-ray detector to face each other with an imaging subject interposed therebetween; controlling the X-ray imaging device to perform a first X-ray imaging with a first dose in a partial section of a rotation locus and to perform a second X-ray imaging with a second dose lower than the first dose in a remaining section while rotating the X-ray emitter and the X-ray detector about a rotating axis between the X-ray emitter and the X-ray detector; and producing an X-ray image by processing first and second X-ray image data of the first and the second X-ray imaging from the X-ray detector.

Advantageous Effects

According to the present invention, it is possible to produce not only a general CT image but also other kinds of modality images by using an X-ray imaging device including an X-ray emitter and an X-ray detector performing X-ray imaging by rotating while facing each other with an imaging subject interposed therebetween, for example, by using a CT imaging device. Accordingly, a separate X-ray imaging device or an integrated X-ray imaging device is not required to produce each of multiple modality images, whereby the cost of X-ray imaging devices is reduced and the X-ray imaging device is simplified, so installation and space utilization are maximized. Accordingly, the efficiency of the X-ray imaging device can be maximized.

In addition, X-ray imaging is controlled to be selectively turned on and off so that X-ray imaging is performed in the predetermined direction required for producing the modality image to be implemented, thereby reducing the X-ray dose and improving the image quality.

Further, an X-ray detector having a small width is used or a partial area of the entire incident area of the X-ray detector is set as the X-ray detection area, whereby the X-ray dose can be reduced and the image quality can be further improved.

MODE FOR INVENTION

Hereinbelow, an exemplary embodiment of the present invention will be described in detail with reference to the accompanying drawings.

Figure 1:
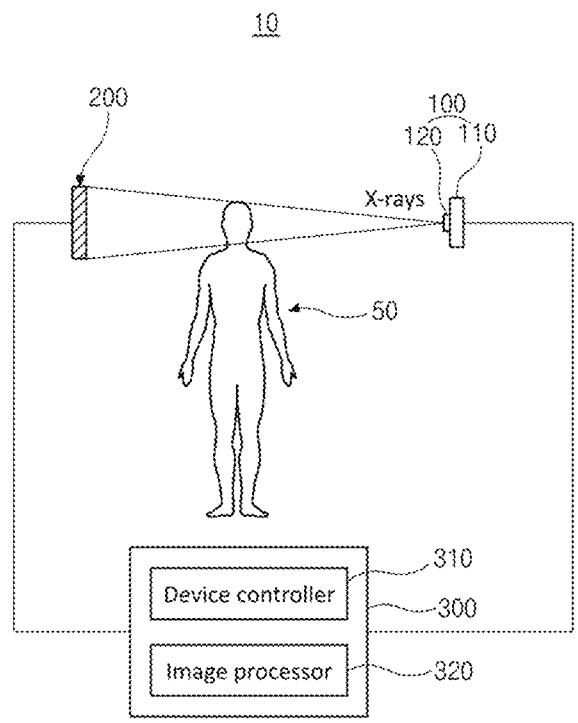
FIG. 1 is a schematic view showing a configuration of an X-ray imaging device according to an embodiment of the present invention.

FIG. 1 is a schematic view showing a configuration of an X-ray imaging device according to an embodiment of the present invention.

Referring to FIG. 1, an X-ray imaging device 10 according to the embodiment of the present invention is a device that produces multi-modality image including a CT image, and is configured to rotate an X-ray emitter and an X-ray detector disposed to face each other with an imaging subject interposed therebetween, about a rotating axis therebetween, whereby it is possible to produce all required kinds of modality images through an X-ray imaging method in which X-ray imaging is performed in various directions with respect to the imaging subject, for example, through CT imaging method.

Accordingly, the device cost for producing a multi-modality image can be reduced, the device design can be simplified, and the efficiency can be maximized.

The X-ray imaging device 10 may include an X-ray emitter 100, an X-ray detector 200, and a device control system 300.

The X-ray emitter 100 is a part that irradiates X-rays, for example, in the form of a cone beam onto an imaging subject 50 interposed between the X-ray detector 200 and the X-ray emitter, wherein the X-ray emitter may include: an X-ray source 110 such as an X-ray tube that generates X-rays; and a collimator 120 disposed at the front of the X-ray source 110 and configured to control a direction of an X-ray beam (i.e. an angle of an X-ray beam) and a width thereof. Herein, by the collimator 120 controlling X-rays, it is possible to adjust the X-ray dose and the position of X-rays irradiated onto the imaging subject 50.

The X-ray detector 200 receives the X-rays having penetrated through the imaging subject 50, and generates image data corresponding to the intensity of the received X-rays. The X-ray detector 200 includes a plurality of pixels arranged in a matrix form in an incident area, and each of the pixels is including a photoelectric conversion element such as a photo diode. Thereby, the X-rays incident on the X-ray detector 200 are detected as an electrical signal in pixel units, and image data can be generated.

Herein, as the X-ray detector 200, a direct conversion type detector, in which a photoelectric conversion element directly detects X-rays, or an indirect conversion type detector, in which X-rays are converted into visible light through a phosphor and a photoelectric conversion element detects the visible light, may be used.

In particular, since the X-ray imaging device 10 according to an embodiment of the present invention is configured to produce various types of modality images including a CT image required by a user, the X-ray detector 200 generates X-ray image data for producing a corresponding modality image.

The device control system 300 may be configured to control the entire operation of the X-ray emitter 100 and the X-ray detector 200 as a whole, and to perform a function of generating a desired modality image based on the X-ray image data generated in the X-ray detector 200.

The device control system 300 may include: a device controller 310 controlling the operation of both the X-ray emitter 100 and the X-ray detector 200; and an image processor 320 receiving X-ray image data generated in the X-ray detector 200 and producing a corresponding modality image by processing the X-ray image data. As for the specific operation of the device controller 310 and the image processor 320, the following description may be referred to.

In the embodiment of the present invention, X-ray data in various directions for the imaging subject is generated and used to produce the modality image desired by the user by using the X-ray imaging device 10 configured as described above, which will be described in more detail hereinbelow.

Figure 2:
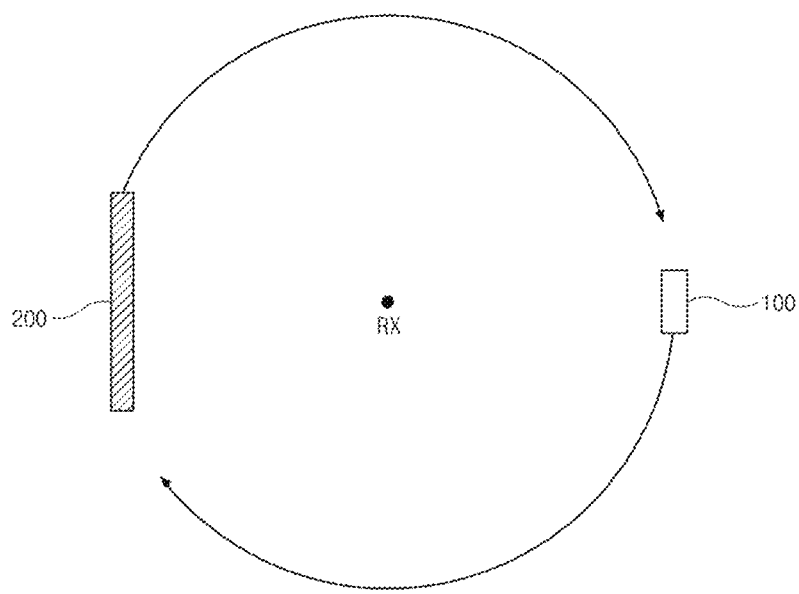
FIG. 2 is a schematic view showing an X-ray emitter and an X-ray detector rotating along a fixed rotating axis during X-ray imaging according to the embodiment of the present invention.

The X-ray imaging device according to an embodiment of the present invention, as shown in FIG. 2, is configured such that the X-ray emitter 100 and the X-ray detector 200 rotate about a fixed rotating axis RX therebetween while facing each other with the imaging subject interposed therebetween. Further, when they rotate about the fixed rotating axis RX, the relative position of the X-ray detector 200, i.e. the relative position with respect to the X-ray emitter 100, is configured to be substantially fixed. Here, depending on the desired type of modality image, the position of the fixed rotating axis RX may be configured to be adjusted.

As described above, in the embodiment of the present invention, the X-ray emitter 100 and the X-ray detector 200 disposed to face each other with the imaging subject interposed therebetween are rotated about the rotating axis RX therebetween, whereby it is possible to produce all required kinds of modality images through an X-ray imaging method in which X-ray imaging is performed in various directions with respect to the imaging subject, for example, through CT imaging method.

Further, as the X-ray detector 200, an X-ray detector 200 for general CT imaging can be used regardless of the type of modality image to be produced. As described above, in the embodiment of the present invention, it is possible to produce all types of modality images using a single detector 200, whereby the efficiency of using the detector can be further maximized compared to the conventional art of individually using the relevant detectors to produce modality images.

Furthermore, in the embodiment of the present invention, it is preferred that X-ray imaging be performed by selectively activating X-ray imaging only for the imaging direction required for producing the desired modality image, of the rotation locus of the X-ray emitter 100 and the X-ray detector 200, and X-ray imaging not be performed by deactivating X-ray imaging for the direction not required for producing the desired modality image. Here, the imaging direction required for producing the desired modality image may be a partial section of the rotation locus of the X-ray emitter 100 and the X-ray detector 200.

Figure 3:
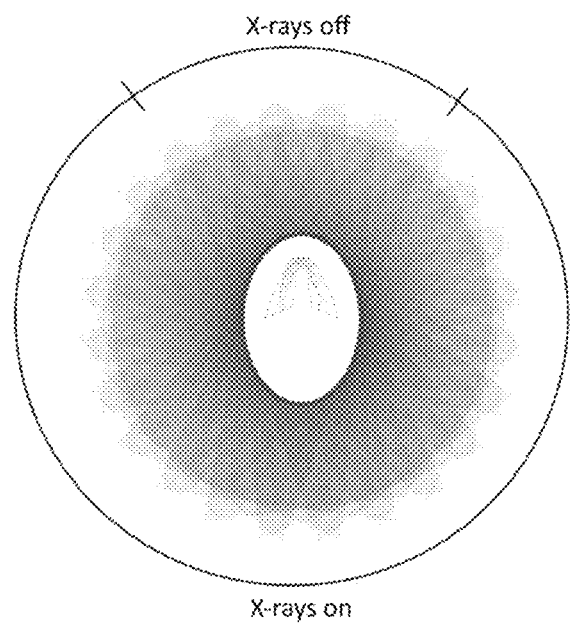
FIG. 3 is a schematic view showing a state where X-ray imaging is selectively performed to produce a dental arch panoramic image according to the embodiment of the present invention.
Figure 4:
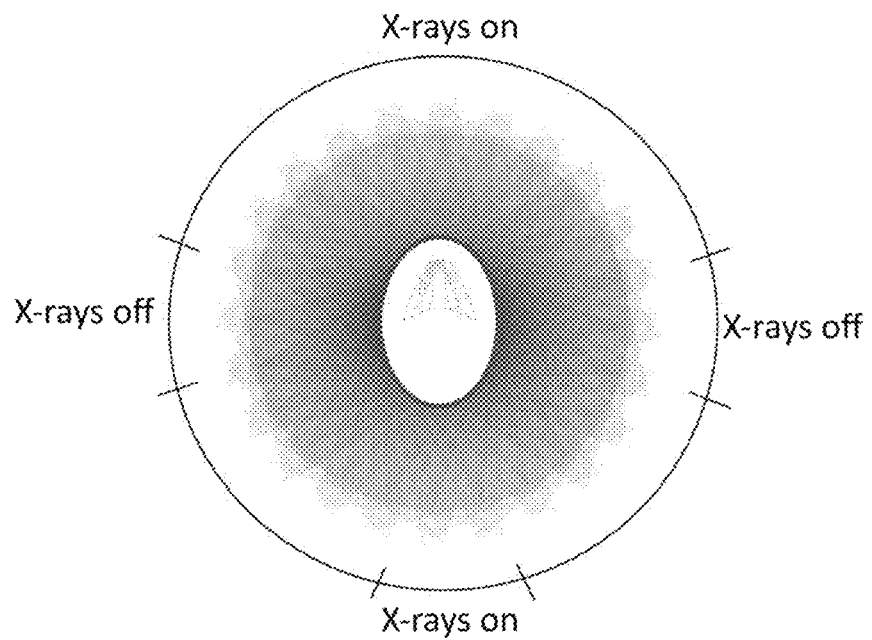
FIG. 4 is a schematic view showing a state where X-ray imaging is selectively performed to produce a posteroanterior (PA) cephalometric image according to the embodiment of the present invention.

The selective X-ray imaging in a partial section of the rotation locus will be described with reference to FIGS. 3 to 5. FIG. 3 is a schematic view showing a state where X-ray imaging is selectively performed to produce a dental arch panoramic image according to the embodiment of the present invention; FIG. 4 is a schematic view showing a state where X-ray imaging is selectively performed to produce a posteroanterior (PA) cephalometric image according to the embodiment of the present invention; and FIG. 5 is a schematic view showing a state where X-ray imaging is selectively performed to produce a lateral (LAT) cephalometric image according to the embodiment of the present invention.

Figure 5:
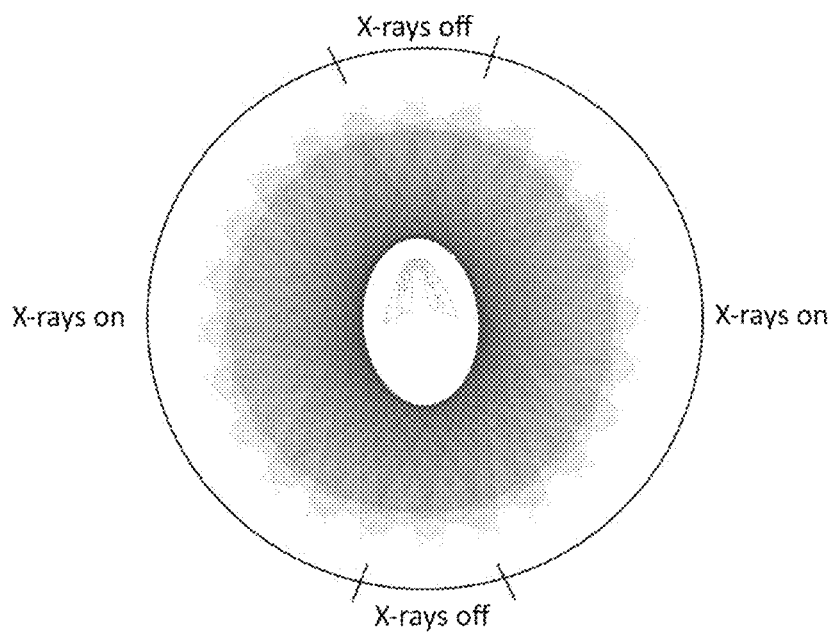
FIG. 5 is a schematic view showing a state where X-ray imaging is selectively performed to produce a lateral (LAT) cephalometric image according to the embodiment of the present invention.

Here, in FIGS. 3 to 5, in rotation of the X-ray emitter 100 and the X-ray detector 200 about the fixed rotating axis with the imaging subject interposed therebetween for X-ray imaging, the X-ray projection in the form of a cone beam marked with blue color (a solid line in the drawing) indicates that the X-ray irradiation is turned off based on the X-ray emitter 100 where the X-ray imaging is not performed, and the X-ray projection in the form of a cone beam marked with red color (a dotted line in the drawing) indicates that X-ray irradiation is on based on the X-ray emitter where the X-ray imaging is performed.

Referring to FIG. 3, in order to produce a dental arch panoramic image, X-ray imaging is performed to detect X-ray image data by turning on the X-ray irradiation in a predetermined direction range (i.e. a predetermined angle) where X-ray projection irradiates the imaging area of the corresponding image, that is, the dental arch, and X-ray imaging is not performed by turning off the X-ray irradiation in the remaining direction range. As described above, the X-ray image data detected in the selective section for the dental arch is processed by the image processor 320 of the device control system 300, whereby it is possible to generate the corresponding dental arch panoramic image.

Here, the section where the X-ray irradiation is selectively turned on to produce the dental arch panoramic image is in a range of 60 to 300 degree angles of the rotation locus of the X-ray emitter and the X-ray detector relative to the front (0 degree angles) of the imaging subject based on the X-ray emitter, whereby X-ray imaging is selectively performed only in the partial section of the rotation locus where the X-ray emitter and the X-ray detector rotate about the rotating axis with the imaging subject interposed therebetween, for example, in the range of 60 to 300 degree angles relative to the front (0 degree angles) of the imaging subject based on the X-ray emitter.

Meanwhile, referring to FIG. 4, in order to produce a PA cephalometric image, X-ray imaging is performed to detect X-ray image data by turning on the X-ray irradiation in a predetermined forward and backward direction range where X-ray projection projects the imaging object of the corresponding image, that is, the head, and X-ray imaging is not performed by turning off the X-ray irradiation in the remaining direction range. As described above, the X-ray image data detected in the selective section for the head is processed by the image processor 320, whereby it is possible to generate the corresponding PA cephalometric image.

Here, the section where the X-ray irradiation is selectively turned on to produce the PA cephalometric image is in a range of 300 to 60 degree angles and 120 to 240 degree angles of the rotation locus of the X-ray emitter and the X-ray detector relative to the front (0 degree angles) of the imaging subject based on the X-ray emitter, whereby X-ray imaging is selectively performed only in the partial section of the rotation locus where the X-ray emitter and the X-ray detector rotate about the rotating axis with the imaging subject interposed therebetween, for example, in the range of 300 to 60 degree angles and 120 to 240 degree angles relative to the front (0 degree angles) of the imaging subject based on the X-ray emitter.

Meanwhile, referring to FIG. 5, in order to produce a LAT cephalometric image, X-ray imaging is performed to detect X-ray image data by turning on the X-ray irradiation in a predetermined lateral direction range where X-ray projection projects the imaging object of the corresponding image, that is, the head, and X-ray imaging is not performed by turning off the X-ray irradiation in the remaining direction range. As described above, the X-ray image data detected in the selective section for the head is processed by the image processor 320, whereby it is possible to generate the corresponding dental arch panoramic image.

Here, the section where the X-ray irradiation is selectively turned on to produce the LAT cephalometric image is in a range of 30 to 150 degree angles and 210 to 330 degree angles of the rotation locus of the X-ray emitter and the X-ray detector relative to the front (0 degree angles) of the imaging subject based on the X-ray emitter, whereby X-ray imaging is selectively performed only in the partial section of the rotation locus where the X-ray emitter and the X-ray detector rotate about the rotating axis with the imaging subject interposed therebetween, for example, in the range of 30 to 150 degree angles and 210 to 330 degree angles relative to the front (0 degree angles) of the imaging subject based on the X-ray emitter.

As described above, according to the embodiment of the present invention, X-ray imaging is selectively performed in a partial section of the rotation locus of the X-ray emitter and the X-ray detector depending on characteristics of a desired modality image, whereby it is possible to produce the corresponding modality image. Accordingly, it is possible to reduce the X-ray dose.

Further, X-ray imaging is performed in the predetermined direction required for producing the modality image to produce the corresponding modality image, whereby it is possible to process an image at a high speed and possible to obtain a high-quality image, which improves diagnostic performance.

In this regard, when X-ray imaging is performed in the entire rotation locus of the X-ray emitter and the X-ray detector, not a partial section thereof, to produce a specific modality image other than a CT image, X-ray image data for the direction other than the predetermined direction required for the desired modality image is also used in image processing, whereby the degradation of the image processing speed is inevitable, and artifacts or blur are caused by image data in undesirable directions, which may cause deterioration of the image quality of the modality image.

Meanwhile, according to the embodiment of the present invention, based on a large-sized CT detector, some of the incident area of the X-ray detector 200 may be used as the X-ray detection area depending on the characteristics of the modality image. In this regard, referring to FIG. 6 related to the panoramic image production, for example, the X-ray detector used for general dental arch panoramic image has a relatively small width compared to that of the CT detector due to the characteristics of the panoramic radiography of the dental arch. Accordingly, in consideration of the characteristics of the panoramic radiography of the dental arch, in the X-ray detector 200 according to the embodiment of the present invention, a partial area of the entire incident area AA is defined as an X-ray detection area DA, and X-ray image data for the detection area DA is detected and transmitted to the image processor 320 of the device control system 300, whereby it is possible to produce the corresponding modality image based thereon.

In addition, the X-ray detector 200 is rotated along a circular arc, and here, the position of the detection area DA may be adjusted according to the position of the X-ray detector 200. In this regard, referring to FIG. 6, for example, in panoramic X-ray imaging of the dental arch using an X-ray detector with the rotating axis fixed, the position of the corresponding X-ray detector changes relative to the X-ray emitter by the characteristics of the dental arch locus. Accordingly, in consideration of the characteristics of the panoramic radiography of the dental arch, in the X-ray detector 200 according to the embodiment of the present invention, the position of the CT imaging detection area DA may be adjusted according to the position of the X-ray detector 200 which rotates along a locus of the circular arc based on the fixed rotating axis RX.

Figure 6:
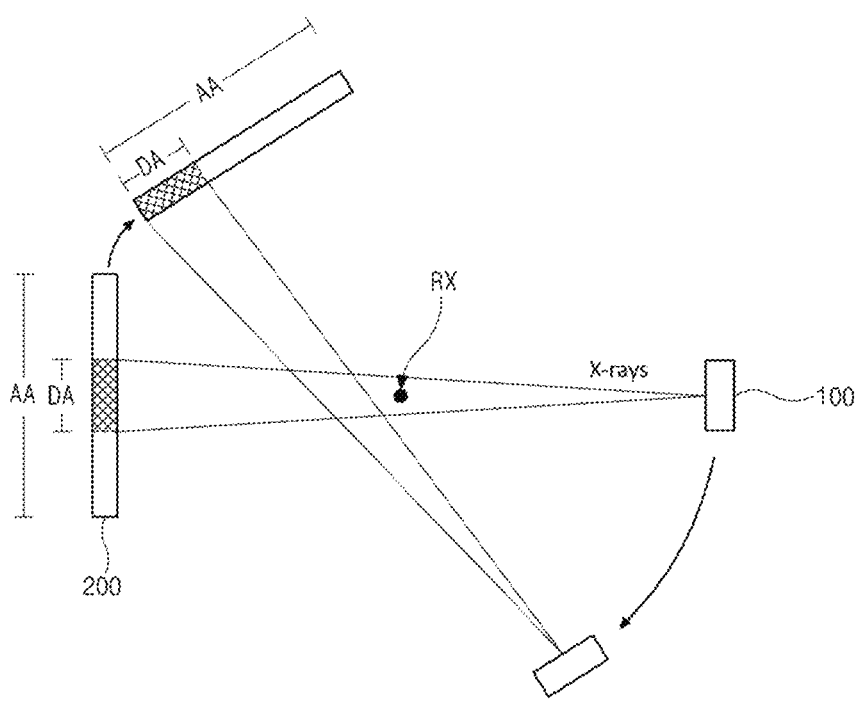
FIG. 6 is a schematic view showing a state where a partial area of the X-ray detector is used as an X-ray detection area and its position is adjusted during X-ray imaging according to the embodiment of the present invention.

Meanwhile, in order to set the partial detection area DA of the X-ray detector 200 and to adjust the detection area DA, as shown in FIG. 6, a width of the X-ray beam irradiated from the X-ray emitter 100 may correspond to the detection area DA and the irradiation angle of the X-ray may be adjusted to correspond to the position of the detection area DA. Adjustment of the width of the X-ray beam of the X-ray emitter 100 and the irradiation angle of the X-ray may be implemented, for example, by controlling the collimator 120 of the X-ray emitter 100.

As described above, a partial area of the entire incident area AA of the X-ray detector 200 is set as the X-ray detection area DA, whereby the X-ray dose can be reduced. In addition, the image data can be acquired in a smaller area unit than in the case of using the entire incident area AA, so that the image quality can be further improved.

Furthermore, not shown in the drawings, the X-ray imaging device according to the present invention may use an X-ray detector having a small width corresponding to the X-ray detection area DA in FIG. 6, for example, an aspect ratio thereof being 1:2 or more and 1:10 or less, instead of the large-sized CT detector. Particularly in this case, the X-ray detector 200 may be moved in a direction of the circular locus or in a tangential direction of the circular locus during the rotation of the X-ray emitter 100 and the X-ray detector 200, or the rotating axis RX may be moved, whereby the same effect as adjusting the position of the detection area DA may be achieved as in FIG. 6.

As described above, according to the embodiment of the present invention, it is possible to produce not only a general CT image but also other kinds of modality images through the X-ray imaging method in which X-ray imaging is performed in various directions with respect to the imaging subject, for example, through the CT imaging method.

Accordingly, a separate X-ray imaging device or an integrated X-ray imaging device is not required to produce a variety of modality images, whereby the cost of X-ray imaging devices is reduced and the X-ray imaging device is simplified, so installation and space utilization are maximized. Accordingly, the efficiency of the X-ray imaging device can be maximized.

In addition, X-ray imaging is controlled to be selectively turned on and off so that X-ray imaging is performed in the predetermined direction required for producing the modality image to be implemented, thereby reducing the X-ray dose and improving the image quality.

Further, a partial area of the entire incident area of the X-ray detector is set as the X-ray detection area or an X-ray detector having a small width is used, whereby the X-ray dose can be reduced and the image quality can be further improved.

Meanwhile, in the above description, it is exemplified that X-ray imaging is selectively performed only in the partial section of the rotation locus where the X-ray emitter and the X-ray detector rotate while facing each other with the imaging subject interposed therebetween. However, if necessary, in the partial section, a first dose of X-rays required for implementing a corresponding modality image may be irradiated from the X-ray emitter, and on the other hand, in the remaining section, where the X-ray irradiation is turned off in the above example, a second dose of X-rays lower than the first dose may be irradiated from the X-ray emitter. Here, the second dose of X-rays may be adjusted, for example, in the range of more than 0% to less than 50% of the first dose of X-rays.

Here, if necessary, as another example, the second dose of X-rays may be in the range of more than 50% to less than 99% of the first dose of X-rays, and in this case, CT images may be acquired for structural analysis rather than for diagnostic purposes for the imaging subject.

For reference, it is well known how to reconstruct multi-modality image from a general CT image, which is performed in such a manner that X-ray imaging result of the imaging subject in various directions is reconstructed to produce a CT image of the imaging subject, and a panoramic image, cephalometric images (PA, LAT, and SMV (submentovertex)), temporo-mandibular joint (TMJ) images (PA and LAT), sinus images (PA and LAT), and the like are reconstructed by using the CT image.

Accordingly, the amount of computation is large, and at least the X-ray dose more than the CT imaging is irradiated onto the imaging subject.

However, in the X-ray imaging device and the X-ray imaging method according to the present invention, X-ray imaging result of the specific section required for the corresponding modality image is obtained, whereby it is possible to produce a desired modality image through the X-ray imaging result without reconstructing a CT image. Further, the X-ray dose irradiated onto the imaging subject during this process is relatively small compared to the CT image, and the amount of computation is also reduced.

As an example, in the case of a dental arch panoramic image, image information on the positional intersection of the locus of the dental arch is arranged or overlapped with each other along the locus of the dental arch by summation of X-ray imaging results of a specific section, thereby producing the dental arch panoramic image. As another example, in the case of a cephalometric image, the cephalometric image can be produced by summation of X-ray imaging results of a specific section in a view direction of the cephalometric image.

The invention claimed is:

1. An X-ray imaging device (10) comprising:
an X-ray emitter (100) and an X-ray detector (200) rotating while facing each other with an imaging subject interposed therebetween along a predetermined rotations locus, wherein the X-ray detector is configured to produce X-ray image data for multi-modality X-ray images including a CT image, a dental arch panoramic image, a posteroanterior cephalometric image, a lateral cephalometric image, a TMJ image, and a sinus image;
a device controller (310) controlling the X-ray imaging device (10) such that an X-ray imaging is performed in at least one section of the rotation locus of the X-ray emitter (100) and the X-ray detector (200) for producing one modality X-ray image selected by a user among the multi-modality X-ray images, wherein a range or a number of the selection varies depending on the modality images; and
an image processor (320) producing said one modality X-ray image by receiving the X-ray image data from the X-ray detector (200).

2. The X-ray imaging device (10) of claim 1, wherein the X-ray emitter (100) is turned off out of the section.

3. The X-ray imaging device (10) of claim 1, wherein the section is in a range of 60 to 300 degree angles relative to a front (0 degree angles) of the imaging subject based on the X-ray emitter (100) when said one modality X-ray image is the dental arch panoramic image of the imaging subject.

4. The X-ray imaging device (10) of claim 1, wherein the partial section is in a range of 300 to 60 degree angles and 120 to 240 degree angles relative to a front (0 degree angles) of the imaging subject based on the X-ray emitter (100) when said one modality is the posteroanterior cephalometric image of the imaging subject.

5. The X-ray imaging device (10) of claim 1, wherein the partial section is in a range of 30 to 150 degree angles and 210 to 330 degree angles relative to a front (0 degree angles) of the imaging subject based on the X-ray emitter (100) when said one modality is the lateral cephalometric image of the imaging subject.

6. The X-ray imaging device (10) of claim 1, wherein the X-ray emitter (100) is configured to adjust a position of the partial area onto which the X-rays are irradiated, according to a location of the X-ray detector (200).

7. The X-ray imaging device (10) of claim 1, wherein the X-ray detector (200) is configured such that an aspect ratio thereof is 1:2 or more and 1:10 or less.

8. The X-ray imaging device (10) of claim 7, wherein the X-ray detector (200) is moved in a direction of the rotation locus or in a tangential direction of the rotation locus during at least a part of the rotation of the X-ray emitter (100) and the X-ray detector (200).

9. The X-ray imaging device (10) of claim 7, wherein a center of the rotation locus of the X-ray emitter (100) and the X-ray detector (200) is moved during at least a part of the rotation of the X-ray emitter (100) and the X-ray detector (200).

10. The X-ray image device (10) of claim 3, wherein the X-ray emitter (100) irradiates X-rays onto a partial area of an entire incident area of the X-ray detector (200).

* * * * *